(12) United States Patent
Brookhart et al.

(10) Patent No.: US 7,030,200 B2
(45) Date of Patent: Apr. 18, 2006

(54) CATALYSTS FOR OLEFIN POLYMERIZATION

(75) Inventors: Maurice Brookhart, Chapel Hill, NC (US); Olafs Daugulis, Carrboro, NC (US)

(73) Assignees: E.I. du Pont de Nemours and Company, Wilmington, DE (US); University of North Carolina, Chapel Hill, NC (US)

( * ) Notice: Subject to any disclaimer, the term of this patent is extended or adjusted under 35 U.S.C. 154(b) by 0 days.

(21) Appl. No.: 10/502,127

(22) PCT Filed: Mar. 5, 2003

(86) PCT No.: PCT/US03/03618

§ 371 (c)(1),
(2), (4) Date: Nov. 10, 2004

(87) PCT Pub. No.: WO03/076450

PCT Pub. Date: Sep. 18, 2003

(65) Prior Publication Data

US 2005/0245702 A1    Nov. 3, 2005

Related U.S. Application Data

(60) Provisional application No. 60/361,998, filed on Mar. 6, 2002.

(51) Int. Cl.
*C07F 15/00*     (2006.01)
*C07F 15/04*     (2006.01)
*C08F 4/70*      (2006.01)

(52) U.S. Cl. .................. 526/172; 526/171; 556/20; 556/32; 556/136; 556/137; 556/146; 556/138; 502/162; 502/167; 502/168

(58) Field of Classification Search ................ 526/171, 526/172; 556/20, 32, 136, 137, 146, 138; 502/162, 168, 167
See application file for complete search history.

(56) References Cited

U.S. PATENT DOCUMENTS

| | | | |
|---|---|---|---|
| 5,929,181 A | 7/1999 | Makovetsky et al. |
| 5,986,027 A | 11/1999 | Lippert et al. |
| 6,177,528 B1 | 1/2001 | LaPointe et al. |
| 6,506,861 B1 | 1/2003 | Wang et al. |

FOREIGN PATENT DOCUMENTS

| | | |
|---|---|---|
| DE | 199 47 519 A1 | 10/1999 |
| JP | 99158213 | 6/1999 |
| JP | 00281710 | 10/2000 |
| WO | WO 98/40420 | 9/1998 |
| WO | WO 99/50313 | 10/1999 |
| WO | WO 00/20377 A1 | 4/2000 |
| WO | WO 00/59956 | 10/2000 |
| WO | WO 01/92347 A2 | 12/2001 |

OTHER PUBLICATIONS

Daugulis et al., "Phosphinidine-Palladium Complexes for the Polymerization and Oligomerization of Ethylene", Oganometallics, 2002, 21, 5935-5943.*

F. Ozawa et. al., Synthesis and Reactions of Palladium and Platinum Complexes Bearing Diphosphinidenecyclobutene Ligands: A Thermally Stable Catalyst for Ethylene Polymerization, Angew. Chem. ITL. Ed. Engl., 2000, p. 4512-4513, vol. 39.

* cited by examiner

*Primary Examiner*—Caixia Lu

(57) ABSTRACT

Late transition metal complexes of certain ligands which contain phosphinidine and/or imine groups are useful as components of polymerization catalysts for olefins. Useful metals in the complexes include Ni, Pd, Fe and Co. Oligomers and/or polymers of olefins such as ethylene can be made.

28 Claims, No Drawings

CATALYSTS FOR OLEFIN POLYMERIZATION

This application claims the benefit of Provisional Application No. 60/361,998, filed Mar. 6, 2002.

FIELD OF THE INVENTION

New late transition metal complexes with neutral ligands useful as catalyst components in the polymerization of olefins, such as ethylene, are described. The ligands contain one or both of the imino and phosphinidine groups.

TECHNICAL BACKGROUND

The (co)polymerization of olefins, especially olefins such as ethylene and propylene by themselves or with other olefins is one of largest parts of the worldwide chemical industry. The resulting polymers are useful in a myriad of ways, and therefore new methods of polymerizing these monomers and/or finding polyolefins with new and different structures are always of interest. Recently it was discovered that certain complexes of late transition metals could be used as part of polymerization catalyst systems for these olefins. Some of these catalyst systems produced polymers with unique structures.

Some of the complexes of late transition metals contained imino groups or various groups containing phosphorous, see for instance U.S. Pat. Nos. 6,177,528 and 5,986,027, World Patent Applications 00/20377, 01/92347, 99/50313,00/59956 and 98/40420, German Patent Application 199 47 519, and Japanese Patent Applications 99158213 and 00281710. None of the ligands and complexes described in these references is claimed herein, either as a composition or as part of a polymerization catalyst system.

The compound designated below as L2 and a complex with Pd is described in M. van der Sluis, et al., *Organometallics*, vol. 16, p. 1144–1152 (1997).

Polymerization of ethylene using phosphinidine-palladium catalysts has been described by F. Ozawa, M. Yoshifuji et. al., *Angew. Chem. Int. Ed. Engl.*, vol. 39, p. 4512 (2000). None of the phosphinidines mentioned in this article are the subject of the present claims.

SUMMARY OF THE INVENTION

This invention concerns a process for the polymerization of olefins, comprising, using a polymerization catalyst system comprising a Ni, Pd, Fe or Co complex of a ligand of the formula

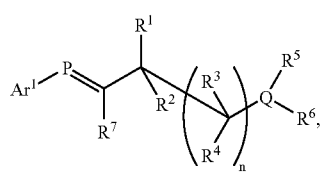

(I)

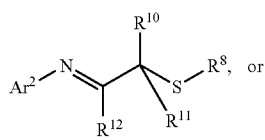

(II)

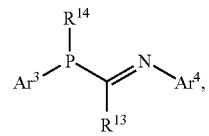

(III)

wherein:

$Ar^1$, $Ar^2$, $Ar^3$ and $Ar^4$ are each independently aryl or substituted aryl;

$R^7$ is hydrogen, hydrocarbyl or substituted hydrocarbyl;

Q is sulfur, oxygen, nitrogen or phosphorous;

n is 0 or 1;

when n is 0 and Q is oxygen or sulfur, $R^1$ and $R^2$ are each independently hydrogen, hydrocarbyl, substituted hydrocarbyl or $R^1$ and $R^2$ taken together form a ring, $R^6$ is not present and $R^5$ is hydrocarbyl or substituted hydrocarbyl;

when n is 1 and Q is oxygen or sulfur, $R^1$, $R^2$, $R^3$ and $R^4$ taken together form an aromatic ring which may be substituted, $R^6$ is not present and $R^5$ is hydrocarbyl or substituted hydrocarbyl;

when n is 0 and Q is nitrogen, $R^1$, $R^2$, $R^5$, $R^6$ and said nitrogen together form an aromatic ring, or $R^1$ is hydrogen, hydrocarbyl or substituted hydrocarbyl, $R^2$ and $R^5$ taken together are part of a double bond, and $R^6$ is aryl or substituted aryl;

when n is 1 and Q is nitrogen, $R^1$ is hydrogen, hydrocarbyl or substituted hydrocarbyl, $R^1$, $R^2$ and $R^3$ are each independently hydrogen, hydrocarbyl or substituted hydrocarbyl provided that any two of $R^1$, $R^2$ and $R^3$ geminal or vicinal to each other together may form a ring, $R^4$ and $R^5$ taken together are part of a double bond, and $R^6$ is aryl or substituted aryl;

when n is 0 and Q is phosphorous $R^1$ and $R^2$ are each independently hydrogen, hydrocarbyl or substituted hydrocarbyl, provided that $R^1$ and $R^2$ taken together may form a ring, and $R^5$ and $R^6$ are each independently hydrocarbyl or substituted hydrocarbyl;

when n is 1 and Q is phosphorous, $R^1$, $R^2$, $R^3$ and $R^4$ taken together form an aromatic ring which may be substituted, and $R^5$ and $R^6$ are each independently hydrocarbyl or substituted hydrocarbyl;

$R^8$ is hydrocarbyl or substituted hydrocarbyl;

$R^{10}$, $R^{11}$ and $R^{12}$ are each independently hydrogen, hydrocarbyl or substituted hydrocarbyl;

$R^{13}$ hydrogen, hydrocarbyl or substituted hydrocarbyl; and $R^{14}$ is hydrocarbyl or substituted hydrocarbyl.

Also disclosed herein is a compound of the formula

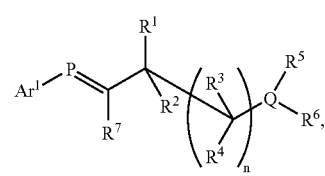

(I)

-continued

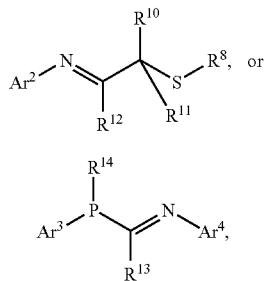
(II)

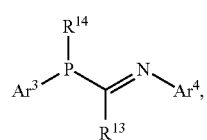
(III)

wherein:

Ar¹, Ar², Ar³ and Ar⁴ are each independently aryl or substituted aryl;

R⁷ is hydrogen, hydrocarbyl or substituted hydrocarbyl;

Q is sulfur, oxygen, nitrogen or phosphorous;

n is 0 or 1;

when n is 0 and Q is oxygen or sulfur, R¹ and R² are each independently hydrogen, hydrocarbyl, substituted hydrocarbyl or R¹ and R² taken together form a ring, R⁶ is not present and R⁵ is hydrocarbyl or substituted hydrocarbyl;

when n is 1 and Q is oxygen or sulfur, R¹, R², R³ and R⁴ taken together form an aromatic ring which may be substituted, R⁶ is not present and R⁵ is hydrocarbyl or substituted hydrocarbyl;

when n is 0 and Q is nitrogen,

R¹, R², R⁵, R⁶ and said nitrogen together form an aromatic ring, or R¹ is hydrogen, hydrocarbyl or substituted hydrocarbyl, R² and R⁵ taken together are part of a double bond, and R⁶ is aryl or substituted aryl;

when n is 1 and Q is nitrogen, R¹ is hydrogen, hydrocarbyl or substituted hydrocarbyl, R¹, R² and R³ are each independently hydrogen, hydrocarbyl or substituted hydrocarbyl provided that any two of R¹, R² and R³ geminal or vicinal to each other together may form a ring, R⁴ and R⁵ taken together are part of a double bond, and R⁶ is aryl or substituted aryl;

when n is 0 and Q is phosphorous R¹ and R² are each independently hydrogen, hydrocarbyl or substituted hydrocarbyl, provided that R¹ and R² taken together may form a ring, and R⁵ and R⁶ are each independently hydrocarbyl or substituted hydrocarbyl;

when n is 1 and Q is phosphorous, R¹, R², R³ and R⁴ taken together form an aromatic ring which may be substituted, and R⁵ and R⁶ are each independently hydrocarbyl or substituted hydrocarbyl;

R⁸ is hydrocarbyl or substituted hydrocarbyl;

R¹⁰, R¹¹ and R¹² are each independently hydrogen, hydrocarbyl or substituted hydrocarbyl;

R¹³ hydrogen, hydrocarbyl or substituted hydrocarbyl; and

R¹⁴ is hydrocarbyl or substituted hydrocarbyl.

Another material disclosed herein is a transition metal complex of a compound of the formula

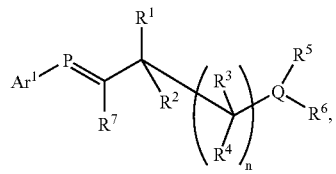
(I)

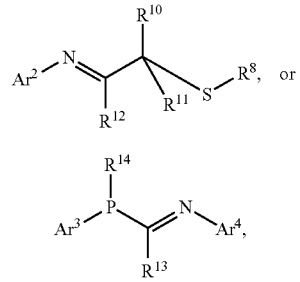
(II)

(III)

wherein:

Ar¹, Ar², Ar³ and Ar⁴ are each independently aryl or substituted aryl;

R⁷ is hydrogen, hydrocarbyl or substituted hydrocarbyl;

Q is sulfur, oxygen, nitrogen or phosphorous;

n is 0 or 1;

when n is 0 and Q is oxygen or sulfur, R¹ and R² are each independently hydrogen, hydrocarbyl, substituted hydrocarbyl or R¹ and R² taken together form a ring, R⁶ is not present and R⁵ is hydrocarbyl or substituted hydrocarbyl;

when n is 1 and Q is oxygen or sulfur, R¹, R², R³ and R⁴ taken together form an aromatic ring which may be substituted, R⁶ is not present and R⁵ is hydrocarbyl or substituted hydrocarbyl;

when n is 0 and Q is nitrogen,

R¹, R², R⁵, R⁶ and said nitrogen together form an aromatic ring, or R¹ is hydrogen, hydrocarbyl or substituted hydrocarbyl, R² and R⁵ taken together are part of a double bond, and R⁶ is aryl or substituted aryl;

when n is 1 and Q is nitrogen, R¹ is hydrogen, hydrocarbyl or substituted hydrocarbyl, R¹, R² and R³ are each independently hydrogen, hydrocarbyl or substituted hydrocarbyl provided that any two of R¹, R² and R³ geminal or vicinal to each other together may form a ring, R⁴ and R⁵ taken together are part of a double bond, and R⁶ is aryl or substituted aryl;

when n is 0 and Q is phosphorous R¹ and R² are each independently hydrogen, hydrocarbyl or substituted hydrocarbyl, provided that R¹ and R² taken together may form a ring, and R⁵ and R⁶ are each independently hydrocarbyl or substituted hydrocarbyl;

when n is 1 and Q is phosphorous, R¹, R², R³ and R⁴ taken together form an aromatic ring which may be substituted, and R⁵ and R⁶ are each independently hydrocarbyl or substituted hydrocarbyl;

R⁸ is hydrocarbyl or substituted hydrocarbyl;

R¹⁰, R¹¹ and R¹² are each independently hydrogen, hydrocarbyl or substituted hydrocarbyl;

R¹³ hydrogen, hydrocarbyl or substituted hydrocarbyl; and

R¹⁴ is hydrocarbyl or substituted hydrocarbyl;

wherein said transition metal is Fe, Co, Ni or Pd;

and provided that when said transition metal is Pd, when n is 0 and Q is nitrogen $R^1$, $R^2$, $R^5$, $R^6$ and said nitrogen together do not form an aromatic ring.

DETAILS OF THE INVENTION

A "hydrocarbyl group" is a univalent group containing only carbon and hydrogen. If not otherwise stated, it is preferred that hydrocarbyl groups (and alkyl groups) herein contain. 1 to about 30 carbon atoms.

By "substituted hydrocarbyl" herein is meant a hydrocarbyl group that contains one or more substituent groups which are inert under the process conditions to which the compound containing these groups is subjected (e.g., an inert functional group, see below). The substituent groups also do not substantially detrimentally interfere with the polymerization process or operation of the polymerization catalyst system. If not otherwise stated, it is preferred that substituted hydrocarbyl groups herein contain 1 to about 30 carbon atoms. Included in the meaning of "substituted" are chains or rings containing one or more heteroatoms, such as nitrogen, oxygen and/or sulfur, and the free valence of the substituted hydrocarbyl may be to the heteroatom. In a substituted hydrocarbyl, all of the hydrogens may be substituted, as in trifluoromethyl.

By "(inert) functional group" herein is meant a group other than hydrocarbyl or substituted hydrocarbyl that is inert under the process conditions to which the compound containing the group is subjected. The functional groups also do not substantially interfere with any process described herein that the compound in which they are present may take part in. Examples of functional groups include halo (fluoro, chloro, bromo and iodo), silyl, and ether such as —$OR^{22}$ wherein $R^{22}$ is hydrocarbyl or substituted hydrocarbyl. In cases in which the functional group may be near a transition metal atom the functional group should not coordinate to the metal atom more strongly than the groups in those compounds are shown as coordinating to the metal atom, that is they should not displace the desired coordinating group.

By "silyl" herein is meant a monovalent group whose free valence is to a silicon atom. The other three valencies of the silicon atom are bound to other groups such as alkyl, halo, alkoxy, etc. Silyl groups are also included in functional groups.

By a "cocatalyst" or a "catalyst activator" is meant one or more compounds that react with a transition metal compound to form an activated catalyst species. One such catalyst activator is an "alkyl aluminum compound" which, herein, is meant a compound in which at least one alkyl group is bound to an aluminum atom. Other groups such as, for example, alkoxide, hydride and halogen may also be bound to aluminum atoms in the compound.

By "neutral Lewis acid" is meant a compound, which is not an ion, which can act as a Lewis acid. Examples of such compounds include boranes, alkylaluminum compounds, aluminum halides, and antimony [V] halides.

By an "empty coordination site" is meant a potential coordination site on a transition metal atom that does not have a ligand bound to it. Thus if an olefin molecule (such as ethylene) is in the proximity of the empty coordination site, the olefin molecule may coordinate to the metal atom.

By a "ligand into which an olefin molecule may insert between the ligand and a metal atom", or a "ligand that may add to an olefin", is meant a ligand coordinated to a metal atom which forms a bond (L—M) into which an olefin molecule (or a coordinated olefin molecule) may insert to start or continue a polymerization. For instance, with ethylene this may take the form of the reaction (wherein L is a ligand):

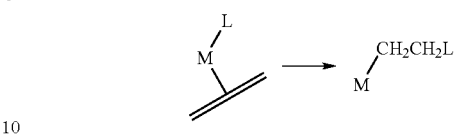

For a summary of which ligands ethylene may insert into (between the ligand and transition metal atom) see for instance J. P. Collman, et al., *Principles and Applications of Organotransition Metal Chemistry*, University Science Books, Mill Valley, Calif., 1987.

By relatively noncoordinating (or weakly coordinating) anions are meant those anions as are generally referred to in the art in this manner, and the coordinating ability of such anions is known and has been discussed in the literature, see for instance W. Beck., et al., *Chem. Rev.*, vol. 88 p. 405–1421 (1988), and S. H. Stares, *Chem. Rev.*, vol. 93, p. 27–42 (1993), both of which are hereby included by reference. Among such anions are those formed from the aluminum compounds in the immediately preceding paragraph and $X^-$, including $R^9{}_3AlX^-$, $R^9{}_2AlClX^-$, $R^9AlCl_2X^-$, and "$R^9AlOX^-$", wherein $R^9$ is alkyl. Other useful noncoordinating anions include BAF-{BAF=tetrakis[3,5-bis(trifluoromethyl)phenyl]borate}, $SbF_6{}^-$, $PF_6{}^-$, and $BF_4{}^-$, trifluoromethanesulfonate, p-toluenesulfonate, $(R_fSO_2)_2N^-$, and $(C_6F_5)_4B^-$.

By a "ligand which may be displaced by an olefin" is meant a ligand coordinated to a transition metal which, when exposed to the olefin (such as ethylene), is displaced as the ligand by the olefin.

By a "neutral ligand" is meant a ligand that is not charged.

"Alkyl group" and "substituted alkyl group" have their usual meaning (see above for substituted under substituted hydrocarbyl). Unless otherwise stated, alkyl groups and substituted alkyl groups preferably have 1 to about 30 carbon atoms.

By "aryl" is meant a monovalent aromatic group in which the free valence is to the carbon atom of an aromatic ring. An aryl may have one or more aromatic rings which may be fused, connected by single bonds or other groups.

By "substituted aryl" is meant a monovalent aromatic group substituted as set forth in the above definition of "substituted hydrocarbyl". Similar to an aryl, a substituted aryl may have one or more aromatic rings which may be fused, connected by single bonds or other groups; however, when the substituted aryl has a heteroaromatic ring, the free valence in the substituted aryl group can be to a heteroatom (such as nitrogen) of the heteroaromatic ring instead of a carbon.

By "$R^x$ and $R^y$ taken together may form a double bond" is meant a structure originally written as —$CRR^x$—$CRR^y$— is, when $R^x$ and $R^y$ do in fact form a double bond, —CR=CR—. In this example each R is simply another group on a carbon atom to satisfy carbon's normal valence requirement of 4.

By a "π-allyl group" is meant a monoanionic ligand comprised of 1 $sp^3$ and two $sp^2$ carbon atoms bound to a metal center in a delocalized $\eta^3$ fashion indicated by

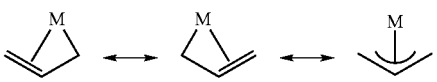

The three carbon atoms may be substituted with other hydrocarbyl groups or functional groups.

By a "hydrocarbon olefin" is meant an olefin containing only carbon and hydrogen.

By an "aromatic ring which may be substituted" is meant an aromatic ring, one or more of whose aromatic hydrogen atoms may be substituted by a substituent (see substituted above) or a functional group. One, some, or all of such hydrogen atoms may be substituted.

By a "polar (co)monomer" or "polar olefin" is meant an olefin which contains one or more elements other than carbon and hydrogen. When copolymerized into a polymer the polymer is termed a "polar copolymer". Useful polar comonomers are found in U.S. Pat. No. 5,866,663, WO 9905189, WO 9909078 and WO 9837110, and S. D. Ittel, et al., *Chem. Rev.*, vol. 100, p. 1169–1203(2000), all of which are incorporated by reference herein for all purposes as if fully set forth. Also included, as a polar comonomer is CO (carbon monoxide).

In the transition metal complexes described herein, one of ligands (I), (II) and (III) is coordinated to a transition metal atom. Ligands (I), (II) and (III), as shown by the above formulas, are neutral ligands. Usually only one molecule of (I), (II) or (III) is coordinated to the transition metal atom. The other coordination sites of the metal atom are usually occupied by other ligands (see below), but one of these coordination sites may be empty. Preferred transition metals are Ni and Pd, and Ni is especially preferred.

One type of preferred monomer are hydrocarbon monomers, such as ethylene and α-olefins of the formula $H_2C=CH-(CH_2)_mCH_3$ wherein m is 0 (propylene) or an integer of 1 to about 20). A preferred monomer is ethylene, or to make a copolymer ethylene and one or more α-olefins. Another type of preferred polymer is a copolymer of ethylene and a polar comonomer (see above). Preferably the polar comonomer is one or both of an acrylate ester and a vinylsilane. Other useful types of monomers include styrenes, norbornenes, and cyclopentenes (all may be substituted with polar or nonpolar groups).

By "polymerization" herein is meant at least two olefin molecules are combined into a single molecule ("dimerized"), or an oligomer or polymer is formed. Preferably the average degree of polymerization (DP, the average number of monomer units in the product molecules) is 5 or more, more preferably about 10 more, and especially preferably about 25 or more. When dimers or other low oligomers are formed they often have internal double bonds and/or branching.

For all purposes herein (both processes and compositions) preferred groups and structures for (I), (II) and (III) are:

$Ar^1$, $Ar^2$, $Ar^3$ and $Ar^4$ are each independently phenyl or substituted phenyl, more preferably substituted phenyl, and especially preferably 2,2,6, or 2,4,6 substituted phenyl, wherein in any of these substituted phenyl groups alkyl groups containing 1–4 carbon atoms are preferred substituents;

when (I) is present $R^7$ is hydrogen;

when (I) is present, when n is 0 and Q is oxygen or sulfur, $R^1$ and $R^2$ are both hydrogen, and $R^5$ is alkyl or substituted alkyl;

when (I) is present, n is 1 and Q is oxygen or sulfur, $R^1$, $R^2$, $R^3$ and $R^4$ taken together form a benzene ring, and $R^5$ is alkyl or substituted alkyl;

when (I) is present, n is 0 and Q is nitrogen, $R^1$, $R^2$, $R^5$, $R^6$ and said nitrogen together form a 2-pyridyl ring (group), or $R^1$ is hydrocarbyl or substituted hydrocarbyl, more preferably phenyl or substituted phenyl, and $R^6$ is phenyl or substituted phenyl, more preferably substituted phenyl, and especially preferably 2,2,6, or 2,4,6 substituted phenyl, wherein in any of these substituted phenyl groups alkyl groups containing 1–4 carbon atoms are preferred substituents;

when (I) is present, n is 1 and Q is phosphorous, $R^1$, $R^2$, $R^3$ and $R^4$ taken together form a benzene ring, and $R^5$ and $R^6$ are each independently aryl or substituted aryl, especially preferably phenyl;

when (I) is present, n is 0 and Q is phosphorous, $R^1$ and $R^2$ are both hydrogen, and $R^5$ and $R^6$ are each independently phenyl or substituted phenyl, more preferably substituted phenyl, and especially preferably 2,2, 6, or 2,4,6 substituted phenyl, wherein in any of these substituted phenyl groups alkyl groups containing 1–4 carbon atoms are preferred substituents;

when (II) is present, $R^{12}$ is hydrogen, $R^{10}$ and $R^{11}$ are each independently hydrocarbyl or substituted hydrocarbyl more preferably alkyl, and especially preferably methyl, and $R^8$ is phenyl or substituted phenyl, more preferably substituted phenyl, and especially preferably 2,2,6, or 2,4,6 substituted phenyl, wherein in any of these substituted phenyl groups alkyl groups containing 1–4 carbon atoms are preferred substituents;

when (III) is present, $R^{13}$ is hydrocarbyl or substituted hydrocarbyl, more preferably phenyl or substituted phenyl, and especially preferably phenyl, and $R^{14}$ is hydrocarbyl or substituted hydrocarbyl, more preferably alkyl.

Within all of the preferred forms of (I), (II) and (III) above any combination of enumerated preferable groups may be chosen to form a preferred compound.

In the polymerization process involving transition metals complexes of (I), (II) and (III), these complexes comprise part or all of a polymerization catalyst system. By comprises or comprising the polymerization catalyst system is meant the catalyst may consist of the metal complex and any other components needed or desired as part of the catalyst system. Depending on the nature of the other "parts" of the transition metal complex, the complex itself may be able, by itself, to cause polymerization of olefin(s), or other components such as one or more co-catalysts and/or activators may also be needed to cause polymerization. For example compounds such as C1 through C16 (see the Examples below) are by themselves "complete" polymerization catalyst systems. These complexes are characterized as having a relatively noncoordinating anion, and ligands which may be displaced by and/or insert an olefin such as ethylene. Such groups include π-allyl groups (C1 and C2), acetonitrile (which can be displaced by an olefin), and methyl groups (into which an olefin can insert between the methyl group and the metal atom). Many of these types of compounds are well known. For example see analogous types of complexes with α-diimines in U.S. Pat. No. 5,880,241, which is hereby included by reference.

However as mentioned above certain complexes require activators. For example, one such type of complex may be

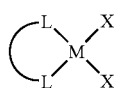
(IV)

wherein each X is a halide anion and

represents the ligand (I), (II) or (III), which in fact may be bidentate. In order for (IV) to be catalytically active it needs to be converted to a complex which has at least one ligand to which an olefin group can add, and one ligand which can be displaced by an olefin or open coordination site to which an olefin may bind to the metal. This can be accomplished by adding to (IV) a compound which can alkylate the metal in (IV), i.e. convert X to alkyl, and which in addition a strong enough Lewis acid to abstract one of the alkyl groups from M to form a relatively noncoordinating anion and an empty coordination site on M. This can be done for example by reacting (IV) with an alkylaluminum compound. In actual polymerization processes this is often done in situ in the polymerization reactor itself, by adding (IV) and the alkylaluminum to the reactor. There are many other methods of activating transition metal complexes for use as olefin polymerization catalysts, see for example U.S. Pat. No. 5,880,241 which describes methods applicable to the complexes described herein.

During the polymerization itself certain compounds containing the transition metal complex and which are active in the polymerization, and which may be termed intermediates may also be formed. For example a compound of the formula

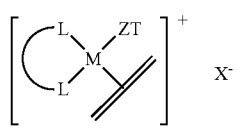
(V)

may be an active intermediate in the polymerization (in this case of ethylene). In (V) Z is a polymethylene chain of indeterminate length formed by the polymerization of ethylene, T was the original group on the complex into which ethylene could insert, and ══is an ethylene molecule. The ethylene molecule may insert in between M and Z thereby adding another monomer unit to the polymer chain, and another ethylene molecule may coordinate to M. This propagation cycle builds up the molecular weight of the polymer being formed. Analogous intermediates with other ligands (for example α-dimines) are found in U.S. Pat. No. 5,880,241, where the present (I), (II) and (III) may be substituted for the α-dimines shown in structures in U.S. Pat. No. 5,880,241.

In the polymerization process herein, the temperature at which the polymerization is carried out is about −100° C. to about +200° C., preferably about −20° C. to about 120° C., more preferably about 0° C. to about 100° C. The pressure of the ethylene or other gaseous olefin at which the polymerization is carried out is not critical, atmospheric pressure to about 275 MPa being a suitable range.

The polymerization process herein may be run in the presence of various liquids, particularly aprotic organic liquids. The catalyst system, ethylene or other olefinic monomer, and/or polymer may be soluble or insoluble in these liquids, but obviously these liquids should not prevent the polymerization from occurring. Suitable liquids include alkanes, cycloalkanes, selected halogenated hydrocarbons, and aromatic hydrocarbons. Specific useful solvents include hexane, toluene, benzene, methylene chloride, 1,2,4-trichlorobenzene and p-xylene.

The polymerization process herein may also initially be carried out in the "solid state" by, for instance, supporting the transition metal compound on a substrate such as silica or alumina, activating if necessary it with one or more cocatalysts and contacting it with, say, ethylene. The support may be considered part of the polymerization catalyst system. Alternatively, the support may first be contacted (reacted) with a cocatalysts (if needed) such as an alkylaluminum compound, and then contacted with an appropriate transition metal compound. The support may also be able to take the place of a Lewis or Bronsted acid, for instance an acidic clay such as montmorillonite, if needed. These "heterogeneous" catalysts may be used to catalyze polymerization in the gas phase or the liquid phase. By gas phase is meant that a gaseous olefin is transported to contact with the catalyst particle. In a preferred form of gas phase polymerization the polymerization catalysts and/or polymer formed is in the form of a fluidized bed.

Depending on their properties, the polyolefins made by the processes described herein are useful in many ways. For instance if they are thermoplastics, they may be used as molding resins, for extrusion, films, etc. If they are elastomeric, they may be used as elastomers. If they contain functionalized monomers such as acrylate esters or other polar monomers, they are useful for other purposes, see for instance previously incorporated U.S. Pat. No. 5,880,241.

Depending on the polymerization process conditions used and the polymerization catalyst system chosen, the polyolefins may have varying properties. Some of the properties that may change are molecular weight and molecular weight distribution, crystallinity, melting point, and glass transition temperature. Except for molecular weight and molecular weight distribution, branching can affect all the other properties mentioned, and branching may be varied (using the same metal complex) using methods described in previously incorporated U.S. Pat. No. 5,880,241.

The present polymerization process may be a batch, semibatch, continuous, gas phase, solution or liquid slurry etc. type process. For example in a continuous gas phase polymerization process the catalyst system is typically supported on a solid particulate support such as silica or alumina, and fluidized bed-like conditions may be employed. Supportation of metal complexes for polymerization catalysts is known in the art, and such methods for supportation which are known may be used with the present catalysts. Hydrogen or other compounds known to be chain transfer agents may be used for polymer molecular weight control. More than two polymerization catalyst systems may be used with the present catalysts. For example one of the polymerization systems may employ the catalysts described herein, which another polymerization system may be a second system as described herein, another late transition metal polymerization catalyst system, a Ziegler-Natta-type polymerization catalyst system or a metallocene-type polymerization system. More than two such polymerization catalyst systems may be employed. Polymerization processes employing two or more polymerization catalyst systems may produce polyolefin blends which have advantageous properties over single polymers.

In the Examples all the operations related to catalysts or phosphines were carried out under an argon atmosphere. Anhydrous solvents were used in the reactions. Solvents were distilled from drying agents or passed through alumina columns under an Ar or $N_2$ atmosphere. The $^1H$ and $^{31}P$ spectra were recorded using a Bruker® 300 or 400 MHz spectrometer and referenced against residual solvent peaks ($^1H$) or $H_3PO_4$ ($^{31}P$). Branching (measuring methyl groups) per 1000 carbon atoms was determined from $^1H$ spectra. Flash chromatography was performed using 60 Å silica gel (SAI). Room temperature GPC measurements were performed on a Waters Alliance® HPLC Separations Module equipped with a Waters Styragel® HR2, HR4, and HR5 columns in series and a Waters® 2410 Differential Refractometer RI (refractive index) detector relative to polystyrene standards. Samples consisted of ~1 mg polymer in 1 mL of degassed THF. High temperature (135° C.) GPC in 1,2,4-trichlorobenzene using a Waters HPLC equipped with Shodex® columns. A calibration curve was established with polystyrene standards.

The following compounds were made using published methods:

[Ni($C_3H_5$)Cl]$_2$—G. Wilke et. al., *Angew. Chem. Int. Ed. Engl.* 1966, 5, 151.

2,2'-Dimethoxybenzophenone: J. W. Altschuld et. al., *J. Organometal. Chem.* 1967, 9, 193.

Dimesitylphosphine: J. B. Lambert et. al., *J. Org. Chem.*, 1991, 56, 5960.

(2,4,6-Triisopropylphenyl)methylphosphine: C. Krüger et. al., *Z. Naturforsch.* 1996, 51b, 1183.

2,4,6-Triisopropylthiophenol: A. J. Costanza et. al., *J. Polymer Sci.* 1955, 17, 1955.

(E)-((2-Pyridyl)methylene) (2,4,6-tri-tert-butylphenyl) phosphine (L2) and its methylpalladium chloride complex: F. Bickelhaupt. et. al., *Organometallics*, 1997, 16, 1144; this method was used also in the synthesis of other phosphinidines (from ketones and aldehydes).

2,4,6-Tri-tert-butylphenylphosphine and 2,4,6-tri-tert-butylphenyldichlorophosphine: A. H. Cowley et. al., *Inorg. Synth.* 1990, 27, 235.

2,4,6-Triisopropylphenylsulfenyl chloride: D. G. Garrat et. al., *Can. J. Chem.* 1980, 58, 2737.

2,6-Diisopropylphenylbenzimidoyl chloride: L. K. Johnson, WO 00/66638.

2,4,6-Triisopropylphenylphosphine: F. Bickelhaupt et. al., *J. Organometal. Chem.* 1991, 405, 183.

2,4,6-Triisopropylphenyldichlorophosphine: G. M. Whitesides et. al., *J. Am. Chem. Soc.* 1974, 96, 5398.

Mesityldichlorophosphine: D. Seebach et. al. *Helv. Chim. Acta* 1993, 76, 2654.

Methylthioacetaldehyde: P. G. Gassman. et. al., *J. Am. Chem. Soc.* 1974, 96, 5495.

(cod)PdMeCl: P. W. N. M. van Leeuwen, K. Vrieze et. al., *Inorg. Chem.* 1993, 32, 5769.

Sulfenylation of aldehyde enolates was carried out according to A. van der Gen et. al., *Tetrahedron Lett.* 1979, 2817.

Synthesis of phosphinidines (HCl elimination method) was carried out according to F. Bickelhaupt et. al., *J. Am. Chem. Soc.* 1978, 100, 4886.

Polymerization of ethylene using phosphinidine-palladium catalysts has been described by F. Ozawa, M. Yoshifuji et. al., *Angew. Chem. Int Ed. Engl.* 2000, 39, 4512.

The following abbreviations are used:

br—branches cod—1,4-cyclooctadiene

GPC—gel permeation chromatography

KHMDS—potassium hexamethyldisilamide

Me—methyl

Mesityl—2,4,6-trimethylphenyl

MMAO—modified methylaluminoxane

Mn—number average molecular weight

Mw—weight average molecular weight

NaBArF$_4$—sodium tetrakis(3,5-bis(trifluoromethyl)phenyl)borate

PDI—Mw/Mn

RT—room temperature

TBSCl—tert-butyldimethylchlorosilane

TBSOLi—lithium dimethyl-t-butylsiloxide

THF—tetrahydrofuran

TLC—thin layer chromatography

TMS—trimethylsilyl

TMSCl—chlorotrimethylsilane

TMSOLi—lithium trimethylsiloxide

TO—turnovers, average number of molecules of ethylene reacted per catalyst molecule TON—turnover number (moles olefin consumed/moles catalyst)

TSOH—p-toluenesulfonic acid

In the Examples given below structures of the various ligands ("L" series) and methyl complexes ("C" series) are given below.

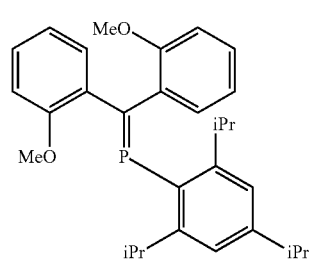

L1

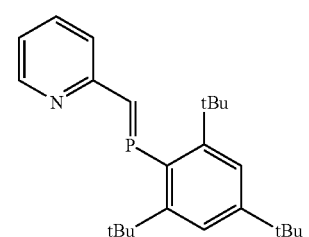

L2

-continued

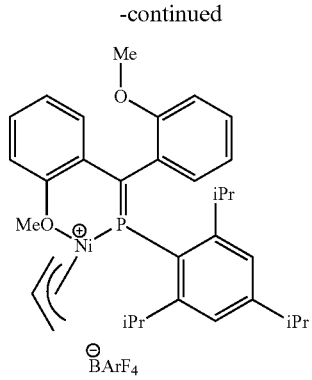

C1

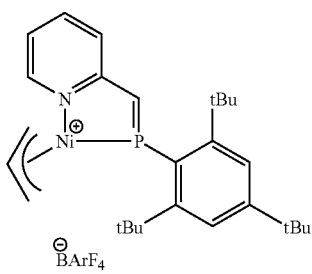

C2

EXAMPLE 1

Synthesis of Ligand L1 n-BuLi (2.0 mL of a 1.6 M solution in hexanes, 3.15 mmol, Aldrich) was added to a solution of 2,4,6-triisopropylphenylphosphine (0.708 g, 3 mmol) in THF (15 mL) at −78° C. The pale yellow solution was stirred at −780° C. for 15 min. Next, a solution of TMSCl (0.40 mL, 3.15 mmol, Aldrich) in THF (1.5 mL) was added dropwise to the solution of (2,4,6-triisopropylphenyl)PHLi at −78° C. over 5 min. The solution was stirred at −78° C. for 10 min, warmed to RT and stirred for 30 min. Assay by $^{31}P$ NMR (crude reaction mixture) showed the formation of the product (−165.5 ppm) together with a minor impurity (−168.6 ppm). The solution was recooled to −78° C. and n-BuLi (2.0 mL of a 1.6 M solution in hexanes, 3.15 mmol, Aldrich) was added to the solution of silylphosphine. The yellow solution was stirred for 10 min at −78° C., warmed to RT and dropwise added to the solution of 2,2'-dimethoxybenzophenone (0.73 g, 3.0 mmol) in THF (40 mL) at −78° C. The resulting solution was stirred for 10 min at −78° C. and then warmed to RT. Upon warming the color changed from yellow to green to yellow to brownish. The solution was stirred for 30 min at RT. The solution was evaporated under Ar, and warm toluene (20 mL) was added to the residue. Inorganic salts were separated by cannula filtration and washed with additional toluene (10 mL). The solution was evaporated under Ar to ca. 5 mL and purified by flash chromatography on silica gel (12×3.4 cm), eluent diethyl ether/hexane 1/3. The fractions containing the product were evaporated and the residue triturated with hexanes (50 mL) to give product as a white powder. Yield 0.89 g (64.5%). $R_f$=0.63 (diethyl ether/hexanes 1/2). $^{31}P\{^{1}H\}$ NMR ($CDCl_3$): +248.5 ppm (s).

EXAMPLE 2

Synthesis of Catalyst C1

A solution of L1 (0.092 g, 0.2 mmol) in toluene (5 mL) was added to a solution of allylnickel chloride dimer (0.028 g, 0.102 mmol) in diethyl ether (5 mL) at −78° C. The solution was stirred at −78° C. for 5 min, warmed to RT and stirred for 10 min. To the resulting mixture a solution of $NaBArF_4$ (0.177 g, 0.2 mmol, Boulder Scientific) in ethyl ether (3 mL) was added. After stirring for 20 min at RT most of the solvent was evaporated and the residue was dissolved in ethyl ether and filtered through Celite®. After evaporation of solvent 0.203 g (71.3%) of dark red solid was obtained. $^{31}P\{^{1}H\}$ NMR ($CD_2Cl_2$): +184.4 ppm (s).

EXAMPLE 3

Synthesis of Catalyst C2

L2 (0.121 g, 0.33 mmol) was mixed with allylnickel chloride dimer (0.045 g, 0.165 mmol) and hexanes (5 mL). The solution was stirred for 1 h, and additional hexanes (5 mL) were added. The violet reaction mixture was stirred for additional 1 h at RT and then the solvent was evaporated. To the violet residue solid $NaBArF_4$ (0.293 g, 0.33 mmol, Boulder Scientific) was added followed by ethyl ether (5 mL). The red-brown reaction mixture was stirred for 3 h at RT, the solution was cannula filtered, and the filtrate was evaporated to give product as a red-brown foam (0.32 g, 72.9%). $^{31}P\{^{1}H\}$ NMR ($CD_2Cl_2$): +256.7 ppm (s).

EXAMPLES 4 AND 5

Polymerizations of Ethylene Using Catalysts C1 and C2

Polymerizations were carried out in a mechanically stirred 300 mL Parr® reactor equipped with an electric heating mantle controlled by a thermocouple in the reaction mixture. The reactor was charged with toluene (100 mL) and heated for 1 h at 150° C. After cooling to RT the solvent was poured out and the reactor heated under vacuum at 150° C. for 1 h. The reactor was filled with Ar, cooled to RT, pressurized to 1.38 MPa ethylene and vented three times. A solution of the catalyst in 100 mL of toluene was added to the reactor via cannula and the reactor heated to the required temperature. After that the reactor was pressurized with ethylene and the reaction mixture stirred for the appropriate time. After venting the reaction mixture was worked up by evaporation of the solvent.

EXAMPLE 4

Polymerization Using Catalyst C1

Eight mg (0.0056 mmol) C1, 30 min at 28° C. followed by 30 min at 100° C., 2.76 MPa ethylene, 40 mg of oligomers. TON=438.

EXAMPLE 5

Polymerization Using Catalyst C2

Fifteen mg (0.011 mmol) C2, 15 min at 30° C., 15 min at 70° C., 20 min at 100° C., then 1 h 100° C. to 65° C., 2.76 MPa ethylene. Filtered off 35 mg polymer ($T_m$=122.4° C., 21 br/1000 C), from toluene additional polymer (100 mg) was isolated by evaporating the solvent. TON=438.
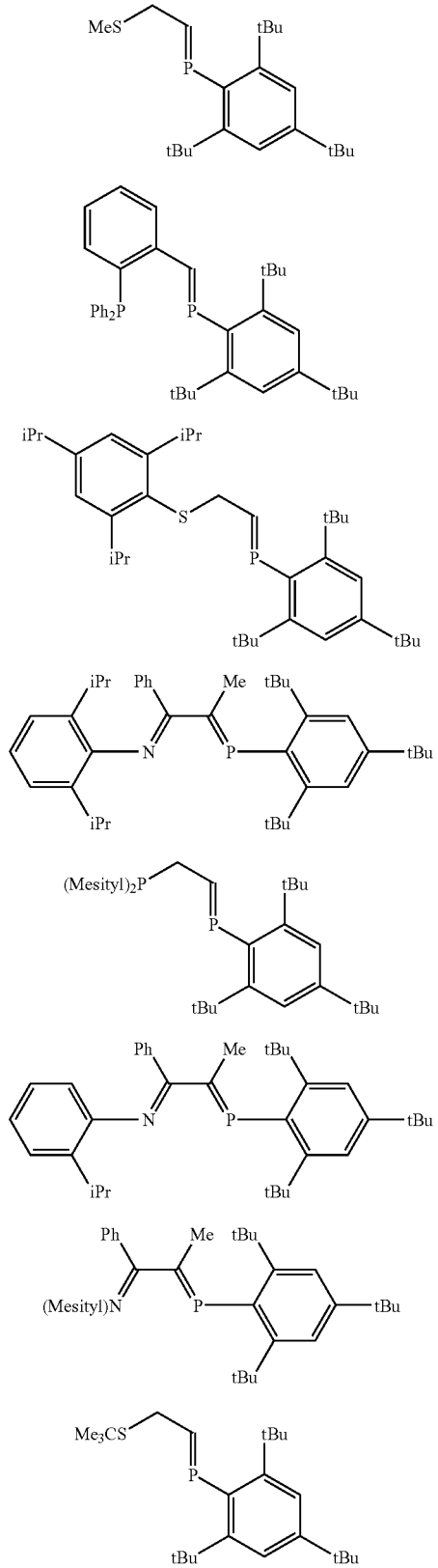
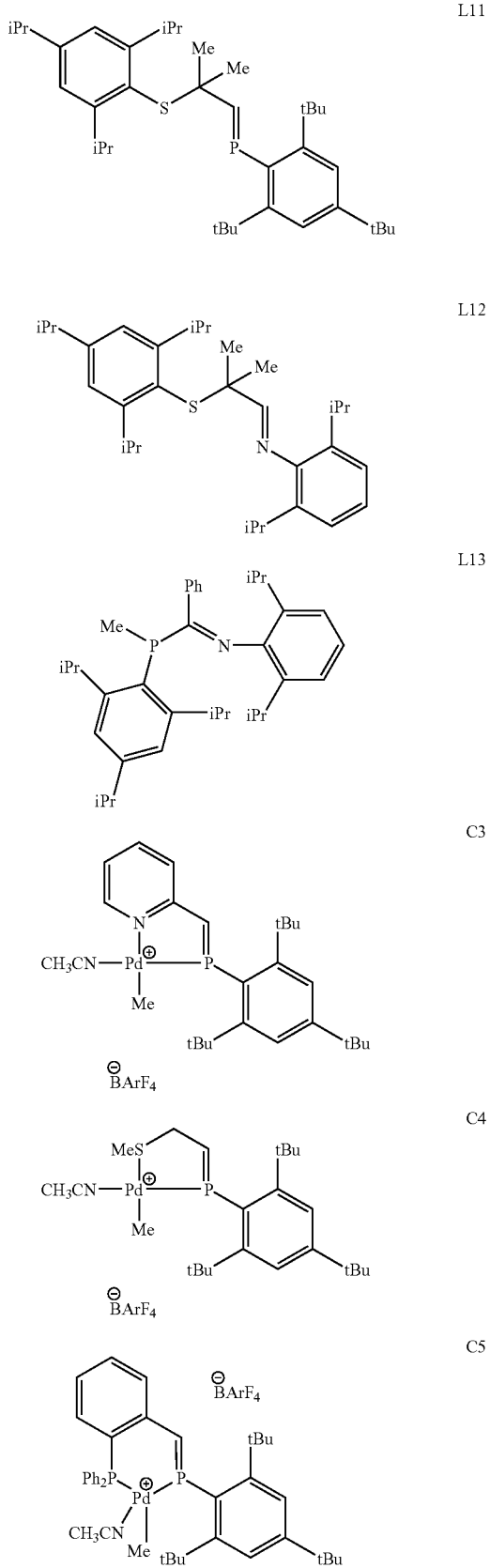

-continued

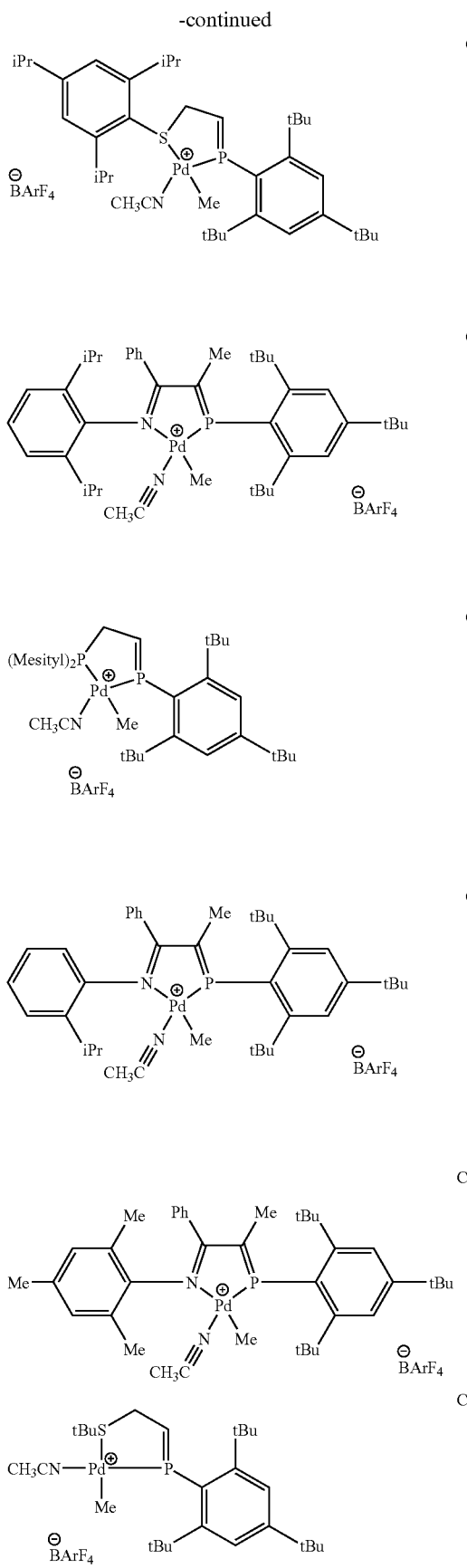

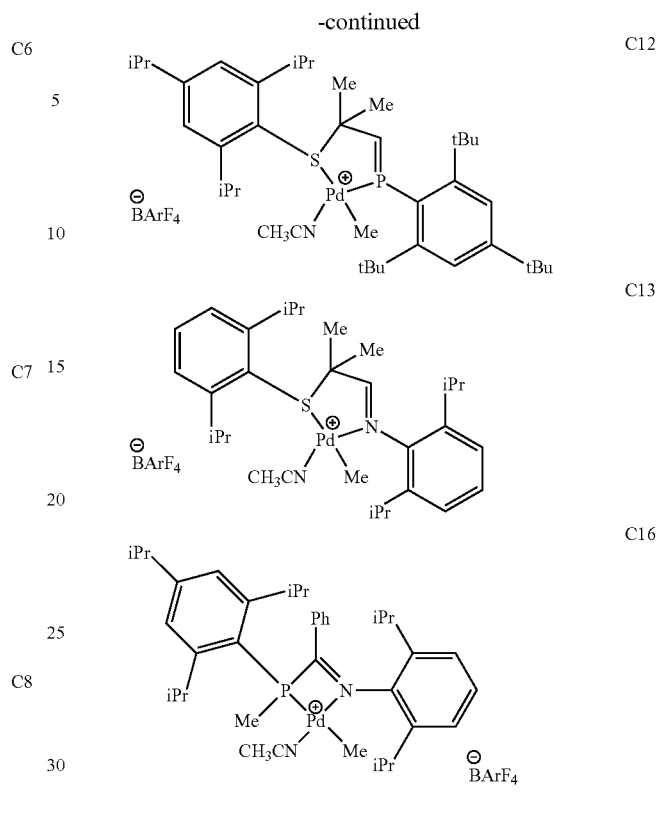

EXAMPLE 6

Preparation of 2,4,6-Tritertbutylphenyl P(Li)SiR$_3$ n-BuLi (2.6 mL of a 1.6 M solution in hexanes, 4.2 mmol, Aldrich) was added to the solution of 2,4,6-tri-t-butylphenylphosphine (1.11 g, 4 mmol) in THF (30 mL) at −78° C. The yellow suspension was stirred at −78° C. for 10 min, warmed to RT and stirred for additional 15 min. A dark red solution was formed. Next, a solution of TBSCl (0.63 g, 4.2 mmol, Aldrich) in THF (10 mL) was added to (2,4,6-tri-t-butylphenyl)PHLi over 10 min at 0° C. The resulting yellowish solution was stirred at 0° C. for 20 min, warmed to RT and stirred for 30 min. Assay by $^{31}$P-NMR showed clean formation of (2,4,6-tri-t-butylphenyl)PHTBS (−135.5 ppm). After cooling to −78° C. additional n-BuLi (2.6 mL of a 1.6 M solution in hexanes, 4.2 mmol, Aldrich) was added and the solution was immediately warmed to RT to give a reddish solution of (2,4,6-tri-t-butylphenyl)P(Li)TBS that was used in the phosphinidine synthesis. The preparation of (2,4,6-tri-t-butylphenyl)P(L1)TMS was carried out in an analogous fashion using TMSCl instead of TBSCl and performing the reaction of (2,4,6-tri-t-butylphenyl)PHLi with the silyl chloride at −78° C.

EXAMPLE 7

Preparation of Catalyst C3

To the mixture of L2(PdMeCl) (prepared from 0.33 mmol ligand, 0.33 mmol (cod)PdMeCl) and NaBArF$_4$ (0.292 g, 0.33 mmol, Boulder Scientific)) was added dry acetonitrile (1 mL) and CH$_2$Cl$_2$ (3 mL). The mixture was stirred for 1 h at RT, cannula filtered to remove NaCl and evaporated. The product was obtained as a yellowish solid (0.405 g, 88.1%). $^{31}P\{^1H\}$ NMR ($CD_2Cl_2$): +248.2 ppm (s).

EXAMPLE 8

Synthesis of Ligand L3

A solution of (methylthio)acetaldehyde (0.198 g, 2.2 mmol) in THF (7 mL) was added dropwise to a solution of ArP(TBS)Li prepared from 2,4,6-tri-t-butylphenylphosphine (2 mmol) at −78° C. The reaction color changed from red to violet at the end of the reaction. After stirring for 30 min at −78° C. the reaction was warmed to RT. Assay by $^{31}P$ NMR showed the presence of phosphinidine isomers in the ratio of 100/12 (+257.3; +250.1). TMSCl (0.3 mL) was added to quench TBSOLi, the solution was evaporated and the residue purified by flash chromatography on silica gel (12×3.3 cm) in pentane. Fractions containing the major isomer were evaporated to give a colorless oil (0.431 g) that slowly crystallized. After recrystallization from dry acetonitrile at −30° C. colorless crystals (0.353 g, 50.4%) were obtained.

EXAMPLE 9

Preparation of Catalyst C4

L3 (0.116 g, 0.33 mmol) was mixed with (cod)PdMeCl (0.088 g, 0.33 mmol) and $CH_2Cl_2$ (3 mL). The yellowish solution was stirred for 1 h at RT. After evaporation the residual oil was triturated with hexanes (3 mL). The hexanes were evaporated and the residue dried under vacuum to give the (phosphinidine)palladium methyl chloride complex as a yellowish solid. It was converted to the cationic acetonitrile complex C4 in the same way as C3. Yield 0.415 g (91.4%), reddish powder. $^{31}P\{^1H\}$ NMR ($CD_2Cl_2$): +231.9 ppm (s).

EXAMPLE 10

Synthesis of Ligand L4

A solution of dry 2-diphenylphosphinobenzaldehyde (0.61 g, 2.1 mmol, Aldrich) in THF (7 mL) was added dropwise to a solution of ArP(TBS)Li prepared from 2,4,6-tri-t-butylphenylphosphine (2 mmol) at −78° C. The reaction color changed from red to brown at the end of the reaction. After stirring for 30 min at −78° C. the reaction was warmed to RT. Assay by $^{31}P$ NMR showed the presence of phosphinidine (+267.7 ppm). TMSCl (0.3 mL) was added to quench TBSOLi, the solution was evaporated and the residue purified by flash chromatography on silica gel (10.5×3.3 cm) in hexane followed by $CH_2Cl_2$/hexane 1/5. Fractions containing the product were evaporated to give a yellow foam (0.73 g, 66.3%). $R_f$=0.42 ($CH_2Cl_2$/hexane 1/5).

EXAMPLE 11

Preparation of Catalyst C5

The synthesis was performed similarly to the synthesis of C4, using 0.33 mmol L4. Product was obtained as a reddish oil, 0.394 g (75.8%). L4(PdMeCl): $^{31}P\{^1H\}$ NMR ($CD_2Cl_2$): +229.9 ppm (d, J=68.6 Hz); +31.6 ppm (d, J=68.6 Hz). C5: $^{31}P\{^1H\}$ NMR ($CD_2Cl_2$): +215.1 ppm (d, J=70.7 Hz); +33.4 ppm (d, J=70.7 Hz).

EXAMPLE 12

Synthesis of (2,4,6-Triisopropylphenylthio)acetaldehyde

Na (0.35 g, 15 mmol) was added in small pieces under Ar to dry ethanol (7 mL). A solution of 2,4,6-triisopropylthiophenol (3.55 g, 15 mmol) was added to the solution of NaOEt and the resulting mixture stirred for 5 min at RT. Bromoacetaldehyde diethylacetal (2.5 mL, 16.5 mmol, Aldrich) was added dropwise to the solution of Na thiolate and the resulting mixture refluxed for 2 h. After that, it was poured into $H_2O$ (100 mL), extracted with $CH_2Cl_2$ (3×50 mL), the extracts dried ($MgSO_4$), filtered and evaporated (aspirator). The NMR showed the presence of the product and ca. 15% of bromoacetaldehyde diethylacetal impurity. The crude reaction mixture was refluxed with 2% aq. HCl (20 mL) and acetone (30 mL) for 2 h 10 min. The reaction mixture was extracted with $CH_2Cl_2$ (3×50 mL), the extracts were dried ($MgSO_4$), filtered and evaporated. Distillation of the product gave a clear liquid, bp 108–114C/0.5 mm, 3.58 g (85.6%). $^1H$ NMR ($CD_2Cl_2$) 9.57 (t, 1H; J=3.4 Hz); 7.00 (s, 2H); 3.86 (septet, 2H; J=7.1 Hz); 3.33 (d, 2H; J=3.4 Hz); 2.87 (septet, 1H; J=7.0 Hz); 1.23 (d, 6H; J=7.0 Hz); 1.22 (d, 12H; J=7.1 Hz).

EXAMPLE 13

Synthesis of L5

A solution of (2,4,6-triisopropylphenylthio)acetaldehyde (0.584 g, 2.1 mmol) in THF (7 mL) was dropwise added to a solution of (2,4,6-tri-t-butylphenyl)P(TBS)L1 prepared from 2,4,6-tritertbutylphenylphosphine (2 mmol) at −78° C. The reaction color changed from red to yellow at the end of the reaction. After stirring for 30 min at −78° C. the reaction was warmed to RT. Assay by $^{31}P$ NMR showed the presence of phosphinidine isomers in the ratio of 100/8 (+262.5; +254.1 ppm). TMSCl (0.3 mL) was added to quench TBSOLi, the solution was evaporated and the residue purified by flash chromatography on silica gel (18×3.3 cm) in hexane. Fractions containing the major isomer were evaporated to give a colorless oil that was dissolved in hexanes (1 mL) and left in the freezer at −30° C. After 4 days colorless crystals of pure major isomer (0.298 g, 27.7%) were filtered off. Major diastereomer (trans) $R_f$=0.17 (hexane). Minor diastereomer (cis) $R_f$=0.23 (hexane). The ligand is somewhat sensitive to water.

EXAMPLE 14

Preparation of Catalyst C6

The synthesis was performed similar to that of C4, using 0.186 mmol L5. Product was obtained as a reddish powder, 0.25 g (85.9%). L5(PdMeCl): $^{31}P\{^1H\}$ NMR ($CD_2Cl_2$): +238.4 ppm (s). C6: $^{31}P\{^1H\}$ NMR ($CD_2Cl_2$): +231.0 ppm (s).

EXAMPLE 15

Synthesis of Propiophenone 2,6-Diisopropylphenylimine 2,6-Diisopropylaniline (3.8 mL, 20 mmol, Aldrich) was mixed with propiophenone (2.7 mL, 20 mmol, Aldrich) and p-TsOH (0.4 g, 2.1 mmol, Aldrich). The resulting mixture was heated at 205° C. for 1.5 h under a slow stream of Ar to remove $H_2O$ that formed. After cooling to RT the reaction mixture was poured into hexanes (50 mL), filtered, the precipitate was washed with additional hexanes (2×20 mL) followed by the evaporation of the filtrate and distillation of the residue. After the initial fraction of starting materials (80–110° C./0.5 mm) the product was collected as a yellow oil, bp 110–125° C./0.5 mm. Crystallization from methanol at −30° C. it afforded product as yellow crystals (4.3 g, 73.3%). $^1H$ NMR ($CDCl_3$) 7.99–7.91 (m, 2H); 7.54–7.44 (m, 3H); 7.20–7.13 (m, 2H); 7.12–7.04 (m, 1H); 2.78 (septet, 2H; J=6.9 Hz); 2.53 (q, 2H; J=7.7 Hz); 1.21 (d, 6H; J=6.9 Hz); 1.16 (d, 6H; J=6.9 Hz); 0.99 (t, 3H; J=7.7 Hz).

EXAMPLE 16

Synthesis of L6 n-BuLi (3.3 mL of a 1.6 M solution in hexanes, 5.25 mmol, Aldrich) was added to a solution of diisopropylamine (0.77 mL, 5.5 mmol, Aldrich) in THF (5 mL) at −78° C. The solution was stirred for 10 min at −78° C. followed by the addition of a solution of propiophenone 2,6-diisopropylphenylimine (1.47 g, 5 mmol) in THF (7 mL). The cooling bath was removed and the reaction mixture was stirred for 3 h at RT. The solution of lithium azaenolate was added dropwise to a solution of 2,4,6-tri-t-butylphenyldichlorophosphine (1.77 g, 5 mmol, contained some (2,4,6-tri-t-butylphenyl)PBrCl) in THF (10 mL) at −78° C. The reaction mixture was warmed to RT and stirred for 1 h. Assay by $^{31}P$-NMR showed the presence of (2,4,6-tri-t-butylphenyl)P(Cl){2-[1-phenyl-1-(N-2,6-diisopropylphenylimino)]propyl} (+99.8 ppm). The solvent was evaporated under Ar, and dry DBU (1.5 mL, 10 mmol, Aldrich) was added, followed by dry $CH_3CN$ (7 mL). The mixture was heated in a sealed Kontes® flask at 90° C. for 3 h. Assay by $^{31}P$-NMR showed the presence of product and chloro (or bromo) phosphine in a 2.5/1 ratio (+304.0, +87.2 ppm) together with some unidentified decomposition products. The solvent was evaporated and the residue filtered through a 10×3.3 cm silica gel column in toluene, collecting the red-yellow product band. After evaporation the residue was recrystallized from $CH_3CN$ twice at −30° C. to give product as red-yellow crystals, 0.88 g (31.0%). $R_f$=0.53 (toluene/hexane 1/1).

EXAMPLE 17

Preparation of Catalyst C7

The synthesis was performed in a similar manner as the synthesis of C4, using 0.176 mmol L6. Product was obtained as a yellowish powder, 0.27 g (96.3%). L6(PdMeCl): $^{31}P\{^1H\}$ NMR ($CD_2Cl_2$): +268.7 ppm (s). C7: $^{31}P\{^1H\}$ NMR ($CD_2Cl_2$): +267.4 ppm (s).

EXAMPLE 18

Synthesis of (Dimesitylphosphino)acetaldehyde

KHMDS (35 mL of a 0.5 M solution in toluene, 17.5 mmol, Aldrich) 35 was added to a solution of dimesitylphosphine (4.1 g, 15.8 mmol) in THF (50 mL) at −78° C. After stirring for 20 min at −78° C. bromoacetaldehyde diethylacetal (2.85 mL, 19 mmol, Aldrich) was added dropwise to the solution of potassium phosphide. The solution was stirred for 5 min at −78° C., warmed to RT and stirred for 30 min at RT. Assay by $^{31}P$-NMR (crude reaction mixture) showed the formation of product (−29.5 ppm). The solvent was evaporated, the residue was flushed through a 6×3.3 cm plug of silica gel and toluene was removed (aspirator) to afford the product as a yellow oil. The product was dissolved in a mixture of degassed acetone (60 mL) and 5% aq. HCl (30 mL) and refluxed under Ar for 2.5 h. A saturated, degassed solution of $NaHCO_3$ (100 mL) was added to the reaction mixture followed by extraction with degassed $CH_2Cl_2$ (3×50 mL). The solution was evaporated under Ar followed by filtration through a plug of silica gel (9×3.6 cm; Ar atmosphere), $CH_2Cl_2$ eluent, collecting 250 mL. Evaporation afforded product as a very air-sensitive white solid, 4.1 g (83.1%). $^{31}P\{^1H\}$ NMR ($CD_2Cl_2$): −35.6 ppm (s).

EXAMPLE 19

Synthesis of L7

A solution of (dimesitylphosphino)acetaldehyde (0.656 g, 2.1 mmol) in THF (10 mL) was dropwise added to a solution of (2,4,6-tri-t-butylphenyl)P(TMS)Li prepared from 2,4,6-tri-t-butylphenylphosphine (2 mmol) at −78° C. The reaction color changed from red to yellow at the end of the reaction. After stirring for 20 min at −78° C. the reaction was warmed to RT. Assay by $^{31}P$ NMR showed the presence of phosphinidine isomers in the ratio of 100/30 (+257.8; +255.9). TMSCl (0.3 mL) was added to quench TMSOLi, the solution was evaporated and the residue purified by flash chromatography on silica gel (16×3.3 cm) in degassed hexane/toluene 15/1 under Ar atmosphere. Fractions containing the major isomer were evaporated to give colorless oil that was recrystallized from hexanes (1 mL) at −30° C. Colorless crystals (0.197 g, 17.2%) were obtained. Major diastereomer (trans) $R_f$=0.17 (hexane). $^{31}P\{^1H\}$ NMR ($CDCl_3$): +257.8 ppm (d, J=54.7 Hz); −19.7 ppm (d, J=54.7 Hz). The ligand is somewhat sensitive to water and oxygen.

EXAMPLE 20

Preparation of Catalyst C8

The synthesis was performed in a manner similar to that of C4, using 0.175 mmol L7. Product was obtained as a reddish oil, 0.25 g (95.8%). L7(PdMeCl) was obtained as a 6/1 isomer mixture. Major isomer: $^{31}P\{^1H\}$ NMR ($CD_2Cl_2$): +251.4 ppm (d, J=11.0 Hz); +35.1 ppm (d, J=11.0 Hz). Minor isomer: $^{31}P\{^1H\}$ NMR ($CD_2Cl_2$): +235.4 ppm (d, J=15.2 Hz); +33.8 ppm (d, J=15.2 Hz). Cationic complex C8 was obtained as a 5/1 isomer mixture. Major isomer: $^{31}P\{^1H\}$ NMR ($CD_2Cl_2$): +242.6 ppm (d, J=14.3 Hz); +34.4 ppm (d, J=14.3 Hz). Minor isomer: $^{31}P\{^1H\}$ NMR ($CD_2Cl_2$): +227.1 ppm (d, J=19.4 Hz); +36.4 ppm (d, J=19.4 Hz).

EXAMPLE 21

Synthesis of Propiophenone 2-Isopropylphenylimine

2-Isopropylaniline (11.6 mL, 82 mmol, Aldrich) was mixed with propiophenone (10 mL, 74.5 mmol, Aldrich) and p-TsOH (1.4 g, 7.3 mmol, Aldrich). The resulting mixture was heated for 2 h at 200° C. under a slow stream of Ar to remove $H_2O$ that formed. After cooling to RT the reaction mixture was poured into hexanes (100 mL), filtered, the precipitate washed with additional hexanes (2×100 mL) followed by the evaporation of the filtrate. The residue was filtered through a 9×4.1 cm plug of silica gel in hexanes/ether 10/1 (300 mL collected). After evaporation of the solvent the residue was distilled in vacuo. The initial fraction contained unreacted starting materials (45–50 C/0.4 mm), in the next fraction the product was collected as an orange oil, bp 125–135 C/0.4 mm, 8.0 g, (42.7%). $^1$H NMR (CDCl$_3$) 8.03–7.95 (m, 2H); 7.53–7.46 (m, 3H); 7.34 (dd, 1H; J=1.4; 7.6 Hz); 7.21 (dt, 1H; J=1.4; 7.6 Hz); 7.1 (dt, 1H; J=1.4; 7.6 Hz); 6.65 (dd, 1H; J=1.4; 7.6 Hz); 3.00 (septet, 1 H; J=6.9 Hz); 2.67 (q, 2H; J=7.6 Hz); 1.22 (d, 6H; J=6.8 Hz); 1.11 (t, 3 H; J=7.6 Hz).

EXAMPLE 22

Synthesis of Ligand L8 n-BuLi (1.3 mL of a 1.6 M solution in hexanes, 2.1 mmol, Aldrich) was added to a solution of diisopropylamine (0.31 mL, 2.2 mmol, Aldrich) in THF (5 mL) at −78° C. The solution was stirred for 10 min at −78° C. followed by the addition of a solution of propiophenone 2-isopropylphenylimine (0.50 g, 2 mmol) in THF (10 mL). The cooling bath was removed and the reaction mixture was stirred for 3 h at RT. The solution of lithium azaenolate was added dropwise to a solution of 2,4,6-tritertbutylphenyldichlorophosphine (0.71 g, 2 mmol; contained some (2,4,6-tri-t-butylphenyl)PBrCl) in THF (10 mL) at −78° C. The reaction mixture was warmed to RT and stirred for 1 h. Assay by $^{31}$P-NMR showed the presence of (2,4,6-tri-t-butylphenyl)P(Cl) ({1-[1-phenyl-1-(N-2,6-diisopropylphenylimino)]propyl} (+91.6 ppm). The solvent was evaporated under Ar, and dry DBU (0.6 mL, 4 mmol, Aldrich) was added, followed by dry CH$_2$Cl$_2$ (10 mL). The mixture was stirred at RT for 155 min. Assay by $^{31}$P-NMR showed the presence of product isomers in a 100/2 ratio (+310.5; +277.6 ppm). The solvent was evaporated and the residue purified by flash chromatography on silica gel (8×3.3 cm) in 1/3 toluene/hexane mixture followed by 1/1 mixture, collecting the red-yellow product band. After evaporation the residue was recrystallized from dry CH$_3$CN at −30° C. to give product as red crystals, 0.39 g (37.4%).

EXAMPLE 23

Preparation of Catalyst C9

The synthesis was performed similar to the synthesis of C4, using 0.19 mmol L8. Product was obtained as a yellowish-green powder, 0.272 g (99.1%). L8(PdMeCl): $^{31}$P{$^1$H} NMR (CD$_2$Cl$_2$): +267.6 ppm (s). C9: $^{31}$P{$^1$H} NMR (CD$_2$Cl$_2$): +266.2 ppm (s).

EXAMPLE 24

Synthesis of Propiophenone 2,4,6-trimethylphenylimine 2,4,6-Trimethylaniline (11.5 mL, 82 mmol, Aldrich) was mixed with propiophenone (10 mL, 74.5 mmol, Aldrich) and p-TsOH (1.4 g, 7.3 mmol, Aldrich). The resulting mixture was heated for 2 h at 200° C. under a slow stream of Ar to remove H$_2$O which formed. After cooling to RT the reaction mixture was poured into hexanes (100 mL), filtered, the precipitate washed with additional hexanes (2×100 mL) followed by the evaporation of the filtrate. The residue was filtered through a 9×4.1 cm plug of silica gel in hexanes/ether 10/1 (300 mL collected). After evaporation of the solvent the unreacted starting materials were distilled off under vacuum (45–50° C./0.4 mm). The residue was crystallized from methanol. Product was isolated as large orange-yellow crystals, 4.8 g, (25.6%). $^1$H NMR (CDCl$_3$) 8.00–7.94 (m, 2H); 7.51–7.45 (m, 3H); 6.89 (s, 2H); 2.50 (q, 2H; J=7.7 Hz); 2.31 (s, 3H); 2.04 (s, 6H); 0.98 (t, 3H; J=7.7 Hz).

EXAMPLE 25

Synthesis of Ligand L9 n-BuLi (2.3 mL of a 1.6 M solution in hexanes, 3.7 mmol, Aldrich) was added to a solution of diisopropylamine (0.54 mL, 3.85 mmol, Aldrich) in THF (10 mL) at −78° C. The solution was stirred for 10 min at −78° C. followed by the addition of a solution of propiophenone 2,4,6-trimethylphenylimine (0.88 g, 3.51 mmol) in THF (15 mL). The cooling bath was removed and the reaction mixture was stirred for 3 h at RT. The solution of lithium azaenolate was added dropwise to a solution of 2,4,6-tritertbutylphenyldichlorophosphine [1.24 g, 3.57 mmol; contained some (2,4,6-tri-t-butylphenyl)PBrCl] in THF (10 mL) at −78° C. The reaction mixture was warmed to RT and stirred for 1 h. Assay by $^{31}$P-NMR showed the presence of ArP(Cl)R (+90.3 ppm). Dry DBU (1.1 mL, 7.36 mmol, Aldrich) was added. After 2 h assay by $^{31}$P-NMR showed no reaction. The solvent was evaporated under vacuum, dry CH$_2$Cl$_2$ (10 mL) and dry CH$_3$CN (10 mL) was added. The mixture was stirred at RT for 15 h 30 min. Assay by $^{31}$P-NMR (crude reaction mixture) showed the presence of product isomers in a 100/4 ratio (+306.7; +279.3 ppm). The solvent was evaporated and the residue filtered through a 16×3.3 cm silica gel plug in CH$_2$Cl$_2$ collecting 100 mL. After evaporation of the solvent the residue was recrystallized from dry CH$_3$CN at −30° C. to give product as yellowish-orange crystals, 1.04 g (57.0%).

EXAMPLE 26

Preparation of Catalyst C10

The synthesis was performed similar to the synthesis of C4, using 0.19 mmol L9. Product was obtained as a yellowish powder, 0.292 g (106%). L9(PdMeCl): $^{31}$P{$^1$H} NMR (CD$_2$Cl$_2$): +267.4 ppm (s). C10: $^{31}$P{$^1$H} NMR (CD$_2$Cl$_2$): +266.0 ppm (s).

EXAMPLE 27

Synthesis of (t-Butylthio)acetaldehyde

KHMDS (100 mL of a 0.5 M solution in toluene, 50 mmol, Aldrich) was added to a solution of 2-methyl-2-propanethiol (5.1 mL, 45.5 mmol, Aldrich) in THF (100 mL) at −78° C. The suspension was warmed to RT, stirred for 30 min followed by the addition of bromoacetaldehyde diethylacetal (7.5 mL, 50 mmol, Aldrich). The reaction was refluxed for 150 min under Ar, water (200 mL) was added and the layers were separated. The aqueous layer was extracted with ethyl ether (100 mL), the combined organic layers were dried (MgSO$_4$), filtered and solvent was evaporated under 1 atm using a Vigreaux column. The residue was distilled under aspirator vacuum. Product was collected at 103–106° C./15 mm. The product was dissolved in acetone-5% aq. HCl mixture (80+40 mL) and refluxed for 2.5 h. After cooling to RT the mixture was extracted with ethyl ether (3×100 mL), dried (MgSO$_4$) and solvent was distilled off using a Vigreaux column. The residue was distilled under aspirator vacuum, bp 63–64° C./15 mm. Yield 2.9 g (48.2%). The compound is unstable and undergoes self-aldol condensation if kept at RT. $^1$H NMR (CDCl$_3$) 9.55 (t, 1H; J=3.2 Hz); 3.27 (d, 2H; J=3.2 Hz); 1.32 (s, 9H).

EXAMPLE 28

Synthesis of Ligand L10

A solution of (t-butylthio)acetaldehyde (0.32 g, 2.4 mmol) in THF (7 mL) was added dropwise to a solution of ArP(TBS)Li prepared from 2,4,6-tritertbutylphenylphosphine (2 mmol) at −78° C. The reaction color changed from red to yellow at the end of the reaction. After stirring for 30 min at −78° C. the reaction was warmed to RT. Assay by $^{31}$P NMR showed the presence of phosphinidine isomers in the ratio of 100/11 (+258.9; +252.8 ppm). TMSCl (0.3 mL) was added to quench TBSOLi, the solution was evaporated and the residue purified by flash chromatography on silica gel (14.5×3.3 cm) in hexane/toluene 15/1 followed by 10/1. Fractions containing the major isomer were evaporated to give colorless oil that slowly crystallized. After recrystallization from dry acetonitrile at −30° C. colorless crystals (0.303 g, 38.6%) were obtained. Major diastereomer (trans) $R_f$=0.16 (hexane/toluene 15/1). Minor diastereomer (cis) $R_f$=0.25 (hexane/toluene 10/1). The ligand is somewhat sensitive to water.

EXAMPLE 29

Preparation of Catalyst C11

The synthesis was performed similar to that of C4, using 0.255 mmol L10. Product was obtained as a reddish foam, 0.29 g (86.7%). L10(PdMeCl): $^{31}$P{$^1$H} NMR (CD$_2$Cl$_2$): +235.3 ppm(s). C11: $^{31}$P{$^1$H} NMR (CD$_2$Cl$_2$): +229.3 ppm (s).

EXAMPLE 30

Synthesis of 2-Methyl-2-(2,4,6-triisopropylphenylthio)propanal

To a suspension of KH (383 mg, 9.5 mmol, Aldrich; washed with hexanes to remove oil and dried in vacuum) in THF (10 mL) was added dropwise isobutyric aldehyde (0.79 mL, 8.7 mmol, Aldrich) in THF (3 mL). The suspension was stirred for 25 min at RT under Ar (evolution of H$_2$). A solution of 2,4,6-triisopropylphenylsulfenyl chloride (2.35 g, 8.7 mmol) in THF (10 mL) was then added at once. The color immediately changed from red to yellow. The solution was stirred at RT for 10 min, water (20 mL) was added to the reaction mixture under Ar (caution —H$_2$ evolution). The solution was extracted with ethyl ether (2×30 mL), the extracts were dried (MgSO$_4$), filtered and evaporated. The residue was purified by flash chromatography on silica gel (13×4.3 cm) in toluene/hexane 1/5 followed by 1/4. Fractions containing the product were evaporated to give a light yellow oil that slowly crystallized, m=2.034 g (68.5%). $R_f$=0.33 (toluene/hexane 1/3). $^1$H NMR (CDCl$_3$) 9.34 (s, 1H); 7.00 (s, 2H); 3.85 (septet, 2H; J=6.9 Hz); 2.86 (septet, 1H; J=6.9 Hz); 1.29 (s, 6H); 1.24 (d, 6H; J=6.9 Hz); 1.18 (unresolved broad d, 12H).

EXAMPLE 31

Preparation of Catalyst C12

A solution of 2-methyl-2-(2,4,6-triisopropylphenylthio) propanal (0.307 g, 1.0 mmol) in THF (5 mL) was added dropwise to a solution of (2,4,6-tri-t-butylphenyl)P(TBS)Li prepared from 2,4,6-tri-t-butylphenylphosphine (1.05 mmol) at −78° C. The reaction color changed from red to light yellow at the end of the reaction. After stirring for 30 min at −78° C. the reaction was warmed to RT. Assay by $^{31}$P NMR showed the presence of phosphinidine (+249.5 ppm). TMSCl (0.2 mL) was added to quench TBSOLi, the solution was evaporated and the residue coevaporated with hexanes (10 mL). A solution of (cod)PdMeCl (0.265 g, 1.0 mmol) in CH$_2$Cl$_2$ (5 mL) was added to the crude phosphinidine and the mixture stirred at RT for 10 h. The color gradually changed from colorless to red-brown. After the evaporation the residue was dissolved in hexanes and purified on a 4×2.3 cm silica gel column, eluting first with hexanes (80 mL) to remove cod and (2,4,6-tri-t-butylphenyl)PH$_2$, then with CH$_2$Cl$_2$ (60 mL) to obtain the product. After evaporation the residue was triturated with hexanes (−30° C.) to give 0.63 g (87.1%) of L11(PdMeCl) as yellow crystals. $^{31}$P{$^1$H} NMR (C6D$_6$): +219.1 ppm(s). The synthesis of cationic acetonitrile complex C12 was performed similar to that of C3 (4 h reaction time), using 0.22 mmol of L11(PdMeCl). Product was obtained as a reddish powder, 0.32 g (91.3%). C12: $^{31}$P{$^1$H} NMR (CD$_2$Cl$_2$): +210.0 ppm (s).

EXAMPLE 32

Synthesis of Ligand L12

To a solution of 2-methyl-2-(2,4,6-triisopropylphenylthio)propanal (0.556 g, 2.0 mmol) in methanol (4 mL) was added formic acid (4 drops) and 2,6-diisopropylaniline (0.76 mL, 4.0 mmol, Aldrich). The reaction was stirred for 20 h at RT. TLC assay showed that reaction was completed at that time. After evaporating solvent the residue was purified by flash chromatography on silica gel (12×3.3 cm) in hexane/toluene 1/1. The solvent in the fractions containing the product was evaporated to give product as a yellowish oil (0.822 g, 88.3%). $R_f$=0.44 (toluene/hexane 1/2). $^1$H NMR (CDCl$_3$) 7.74 (s, 1H); 7.34–7.10 (m, 3H); 7.09 (s, 2H); 4.09 (septet, 2H; J=6.9 Hz); 3.00 (septet, 2H; J=6.9 Hz); 2.94 (septet, 1H; J= 6.9 Hz); 1.52 (s, 6H); 1.31 (d, 6H; J=6.9 Hz); 1.24 (unresolved broad d, 12H); 1.22 (d, 12H; J=6.9 Hz).

EXAMPLE 33

Preparation of Catalyst C13

L12 (0.093 g, 0.2 mmol) was mixed with (cod)PdMeCl (0.053 g, 0.2 mmol) and benzonitrile (2 mL). The reaction mixture was stirred at RT for 5 h followed by evaporation of benzonitrile at 0.2 mm/RT. The complex was isolated as a pale yellow solid. To this material was added NaBArF$_4$ (0.177 g, 0.2 mmol, Boulder Scientific), dry acetonitrile (1 mL) and CH$_2$Cl$_2$ (2 mL) and the residual mixture was stirred for 6 h at RT. After cannula filtration and evaporation the residue was directly used in the polymerization experiments.

EXAMPLE 34

Preparation of Catalyst C16 n-BuLi (0.66 mL of a 1.6 M solution in hexanes, 1.05 mmol, Aldrich) was added to a solution of methyl 2,4,6-triisopropylphenylphosphine (0.25 g, 1.0 mmol) in THF (3 mL) at 0° C. The reaction mixture was stirred at RT for 10 min and then added dropwise to a solution of 2,6-diisopropylphenylbenzimidoyl chloride (0.30 g, 1.0 mmol) in THF (5 mL) at −78° C. The reaction mixture was warmed to RT and stirred for 1 h. Assay by $^{31}$P-NMR (crude reaction mixture) showed the presence of product (−26.2 ppm). The solvent was evaporated, the residue dissolved in toluene and filtered through a pad of Celite®. After evaporation of the solvent a solution of (cod)PdMeCl (0.24 g, 0.91 mmol) in $CH_2Cl_2$ (15 mL) was added. Assay by $^{31}$P-NMR (crude reaction mixture) showed the presence of two product isomers (+15.1; +14.2 ppm, not completely resolved). The solution was evaporated, the residue washed with hexanes (3×10 mL) and dried under vacuum. (L13)PdMeCl was isolated as a yellow powder, 0.495 g (73.9%). It is somewhat light-sensitive.

The synthesis of cationic acetonitrile complex was performed similar to that of C3, using 0.15 mmol (L13) PdMeCl, reaction time 5 h. Product was obtained as a greenish-yellow foam, 0.231 g (100%). $^{31}$P{1H} NMR ($CD_2Cl_2$): −16.0 ppm (br s).

EXAMPLES 35–40

Dimerizations, Oligomerizations and Polymerizations of Ethylene Using Catalysts C3–C14

Initial screening reactions were carried out in NMR tube experiments at RT (0.6 mL $CD_2Cl_2$ solvent, 0.01 mmol catalyst, 20 equiv. ethylene). In the case of C3, C4, C5, C8, C11, and C14 butenes were obtained. C4 and C11 predominately produced cis-2-butene. The reactions with other catalysts were carried out according to general methods described below.

Polymerizations were carried out in a mechanically stirred 300 mL Parr® reactor equipped with an electric heating mantle controlled by a thermocouple in the reaction mixture. The reactor was charged with solvent (100 mL) and heated for 1 h at 150° C. After cooling to RT the solvent was poured out and the reactor heated under vacuum at 150° C. for 1 h. The reactor was filled with Ar, cooled to RT, pressurized to 1.38 MPa ethylene and vented three times. A solution of the catalyst in 100 mL of solvent was added to the reactor via cannula and the reactor cooled to RT. After that the reactor was pressurized with ethylene to 2.76 MPa and the reaction mixture stirred for the appropriate time. After venting the reaction is mixture was worked up by evaporation of the solvent.

EXAMPLE 35

Oligomerization Using Catalyst C6

C6: 0.01 mmol (16 mg), $CH_2Cl_2$ solvent.
Three h run: 3.6 g oligomers isolated (some $C_4$–$C_8$ fraction lost by evaporation of solvent, GC analysis), 4300 TO/h, Mn=215, 64 br/1000 C.
Fifteen h run: 12.5 g oligomers isolated (some $C_4$–$C_8$ fraction lost by evaporation of solvent, GC analysis), 3000 TO/h, Mn=182, 40 br/1000 C.

EXAMPLE 36

Oligomerization Using Catalyst C7

C7: 0.01 mmol (16 mg), $CH_2Cl_2$ solvent.
Three h run: 19 mg oligomers isolated, 23 TO/h, Mn=667.
Fifteen h run: 76 mg oligomers isolated, 18 TO/h, Mn=588.

EXAMPLE 37

Oligomerization Using Catalyst C9

C9: 0.01 mmol (16 mg), toluene solvent.
Three h run: 41 mg oligomers isolated (some $C_4$–$C_8$ fraction presumably lost by evaporation of solvent), 49 TO/h, Mn=452.
Fifteen h run: 111 mg oligomers isolated (some $C_4$–$C_8$ fraction presumably lost by evaporation of solvent), 22 TO/h, Mn=417, 46 br/1000 C.

EXAMPLE 38

Oligomerization Using Catalyst C10

C10: 0.01 mmol (16 mg), $CH_2Cl_2$ solvent.
Three h run: 79 mg oligomers isolated (some $C_4$–$C_8$ fraction lost by evaporation of solvent, GC analysis), 94 TO/h, Mn=303.
Fifteen h run: 273 mg oligomers isolated (some $C_4$–$C_8$ fraction lost by evaporation of solvent, GC analysis), 65 TO/h, Mn=227, 38 br/1000 C.

EXAMPLE 39

Polymerization Using Catalyst C12

C12: 0.01 mmol (16 mg), $CH_2Cl_2$ solvent.
Three h run: 2.6 g polymer isolated, 3100 TO/h, Mn=2297 (NMR), 119 br/1000 C.
Eight h run: 5.2 g polymer isolated, 2300 TO/h, Mn=2528 (NMR), 3596 (GPC), Mw=5261, PDI=1.59, 119 br/1000 C.

EXAMPLE 40

Polymerization Using Catalyst C13

C13: 0.01 mmol (16 mg), $CH_2Cl_2$ solvent.
Three h run: 54 mg polymer isolated, 64 TO/h, Mn=1775.
Fifteen h run: 72 mg oligomers isolated, 17 TO/h, Mn=1624.

The ethylene may have displaced the ligand from the metal.

What is claimed is:

1. A process for the polymerization of olefins, comprising, using a polymerization catalyst system comprising a Ni, Pd, Fe or Co complex of a ligand of the formula

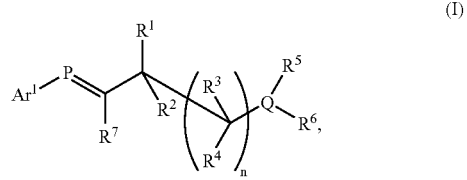

(I)

-continued

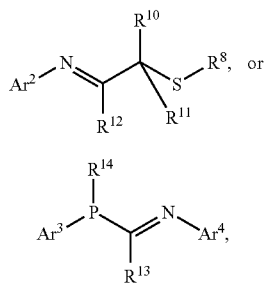

wherein:
Ar$^1$, Ar$^2$, Ar$^3$ and Ar$^4$ are each independently aryl or substituted aryl;
R$^7$ is hydrogen, hydrocarbyl or substituted hydrocarbyl;
Q is sulfur, oxygen, nitrogen or phosphorous;
n is 0 or 1;
when n is 0 and Q is oxygen or sulfur, R$^1$ and R$^2$ are each independently hydrogen, hydrocarbyl, substituted hydrocarbyl or R$^1$ and R$^2$ taken together form a ring, R$^6$ is not present and R$^5$ is hydrocarbyl or substituted hydrocarbyl;
when n is 1 and Q is oxygen or sulfur, R$^1$, R$^2$, R$^3$ and R$^4$ taken together form an aromatic ring which may be substituted, R$^6$ is not present and R$^5$ is hydrocarbyl or substituted hydrocarbyl;
when n is 0 and Q is nitrogen,
R$^1$, R$^2$, R$^5$, R$^6$ and said nitrogen together form an aromatic ring,
or R$^1$ is hydrogen, hydrocarbyl or substituted hydrocarbyl, R$^2$ and R$^5$ taken together are part of a double bond, and R$^6$ is aryl or substituted aryl;
when n is 1 and Q is nitrogen, R$^1$ is hydrogen, hydrocarbyl or substituted hydrocarbyl, R$^1$, R$^2$ and R$^3$ are each independently hydrogen, hydrocarbyl or substituted hydrocarbyl provided that any two of R$^1$, R$^2$ and R$^3$ geminal or vicinal to each other together may form a ring, R$^4$ and R$^5$ taken together are part of a double bond, and R$^6$ is aryl or substituted aryl;
when n is 0 and Q is phosphorous R$^1$ and R$^2$ are each independently hydrogen, hydrocarbyl or substituted hydrocarbyl, provided that R$^1$ and R$^2$ taken together may form a ring, and R$^5$ and R$^6$ are each independently hydrocarbyl or substituted hydrocarbyl;
when n is 1 and Q is phosphorous, R$^1$, R$^2$, R$^3$ and R$^4$ taken together form an aromatic ring which may be substituted, and R$^5$ and R$^6$ are each independently hydrocarbyl or substituted hydrocarbyl;
R$^8$ is hydrocarbyl or substituted hydrocarbyl;
R$^{10}$, R$^{11}$ and R$^{12}$ are each independently hydrogen, hydrocarbyl or substituted hydrocarbyl;
R$^{13}$ hydrogen, hydrocarbyl or substituted hydrocarbyl; and
R$^{14}$ is hydrocarbyl or substituted hydrocarbyl.

2. The process as recited in claim 1 wherein only 1 molecule of said ligand is coordinated to an atom of said transition metal.

3. The process as recited in claim 2 which is carried out at a temperature of about −100° C. to about +200° C.

4. The process as recited in claim 3 wherein said olefin is ethylene alone.

5. The process as recited in claim 4 wherein Ar$^1$, Ar$^2$, Ar$^3$ and Ar$^4$ are each independently phenyl or substituted phenyl.

6. The process as recited in claim 5 wherein said ligand is (I), and said transition metal is Ni.

7. The process as recited in claim 6 wherein:
R$^7$ is hydrogen;
when n is 0 and Q is oxygen or sulfur, R$^1$ and R$^2$ are both hydrogen, and R$^5$ is alkyl or substituted alkyl;
when n is 1 and Q is oxygen or sulfur, R$^1$, R$^2$, R$^3$ and R$^4$ taken together form a benzene ring, and R$^5$ is alkyl or substituted alkyl;
when (I) is present, n is 0 and Q is phosphorous, R$^1$ and R$^2$ are both hydrogen, and R$^5$ and R$^6$ are each independently phenyl or substituted phenyl,
when n is 0 and Q is nitrogen, R$^1$, R$^2$, R$^5$, R$^6$ and said nitrogen together form a 2-pyridyl ring (group), or R$^1$ is phenyl or substituted phenyl, and R$^6$ is phenyl or substituted phenyl; and
when n is 1 and Q is phosphorous, R$^1$, R$^2$, R$^3$ and R$^4$ taken together form a benzene ring, and R$^5$ and R$^6$ are each independently aryl or substituted aryl.

8. The process as recited in claim 5 wherein said ligand is (II) and said transition metal is Ni.

9. The process as recited in claim 8 wherein R$^{12}$ is hydrogen, R$^{10}$ and R$^{11}$ are each independently hydrocarbyl or substituted hydrocarbyl, and R$^8$ is phenyl or substituted phenyl.

10. The process as recited in claim 5 wherein said ligand is (III) and said transition metal is Ni.

11. The process as recited in claim 10 wherein R$^{13}$ is hydrocarbyl or substituted hydrocarbyl, and R$^{14}$ is hydrocarbyl or substituted hydrocarbyl.

12. The process as recited in claim 3 wherein said transition metal is Pd or Ni.

13. A compound of the formula

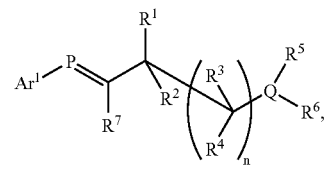

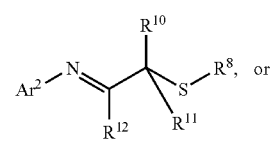

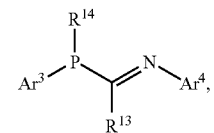

wherein:
Ar$^1$, Ar$^2$, Ar$^3$ and Ar$^4$ are each independently aryl or substituted aryl;
R$^7$ is hydrogen, hydrocarbyl or substituted hydrocarbyl;
Q is sulfur, oxygen, nitrogen or phosphorous;
n is 0 or 1;
when n is 0 and Q is oxygen or sulfur, R$^1$ and R$^2$ are each independently hydrogen, hydrocarbyl, substituted hydrocarbyl or R$^1$ and R$^2$ taken together form a ring, R$^6$ is not present and R$^5$ is hydrocarbyl or substituted hydrocarbyl;

when n is 1 and Q is oxygen or sulfur, $R^1$, $R^2$, $R^3$ and $R^4$ taken together form an aromatic ring which may be substituted, $R^6$ is not present and $R^5$ is hydrocarbyl or substituted hydrocarbyl;

when n is 0 and Q is nitrogen, $R^1$, $R^2$, $R^5$, $R^6$ and said nitrogen together form an aromatic ring, or $R^1$ is hydrogen, hydrocarbyl or substituted hydrocarbyl, $R^2$ and $R^5$ taken together are part of a double bond, and $R^6$ is aryl or substituted aryl;

when n is 1 and Q is nitrogen, $R^1$ is hydrogen, hydrocarbyl or substituted hydrocarbyl, $R^1$, $R^2$ and $R^3$ are each independently hydrogen, hydrocarbyl or substituted hydrocarbyl provided that any two of $R^1$, $R^2$ and $R^3$ geminal or vicinal to each other together may form a ring, $R^4$ and $R^5$ taken together are part of a double bond, and $R^6$ is aryl or substituted aryl;

when n is 0 and Q is phosphorous $R^1$ and $R^2$ are each independently hydrogen, hydrocarbyl or substituted hydrocarbyl, provided that $R^1$ and $R^2$ taken together may form a ring, and $R^5$ and $R^6$ are each independently hydrocarbyl or substituted hydrocarbyl;

when n is 1 and Q is phosphorous, $R^1$, $R^2$, $R^3$ and $R^4$ taken together form an aromatic ring which may be substituted, and $R^5$ and $R^6$ are each independently hydrocarbyl or substituted hydrocarbyl;

$R^8$ is hydrocarbyl or substituted hydrocarbyl;

$R^{10}$, $R^{11}$ and $R^{12}$ are each independently hydrogen, hydrocarbyl or substituted hydrocarbyl;

$R^{13}$ hydrogen, hydrocarbyl or substituted hydrocarbyl; and $R^{14}$ is hydrocarbyl or substituted hydrocarbyl.

14. The compound as recited in claim 13 which is (I).

15. The compound as recited in claim 14 wherein:

$Ar^1$ is phenyl or substituted phenyl;

$R^7$ is hydrogen;

when n is 0 and Q is oxygen or sulfur, $R^1$ and $R^2$ are both hydrogen, and $R^5$ is alkyl or substituted alkyl;

when n is 1 and Q is oxygen or sulfur, $R^1$, $R^2$, $R^3$ and $R^4$ taken together form a benzene ring, and $R^5$ is alkyl or substituted alkyl;

when n is 0 and Q is nitrogen, $R^1$, $R^2$, $R^5$, $R^6$ and said nitrogen together form a 2-pyridyl ring (group), or $R^1$ is phenyl or substituted phenyl, and $R^6$ is phenyl or substituted phenyl;

when (I) is present, n is 0 and Q is phosphorous, $R^1$ and $R^2$ are both hydrogen, and $R^5$ and $R^6$ are each independently phenyl or substituted phenyl, and when n is 1 and Q is phosphorous, $R^1$, $R^2$, $R^3$ and $R^4$ taken together form a benzene ring, and $R^5$ and $R^6$ are each independently aryl or substituted aryl.

16. The compound as recited in claim 13 which is (II).

17. The compound as recited in claim 16 wherein $Ar^2$ is phenyl or substituted phenyl, wherein $R^{12}$ is hydrogen, $R^{10}$ and $R^{11}$ are each independently hydrocarbyl or substituted hydrocarbyl, and $R^8$ is phenyl or substituted phenyl.

18. The compound as recited in claim 13 which is (III).

19. The compound as recited in claim 18 wherein $Ar^3$ and $Ar^4$ are each independently phenyl or substituted phenyl, $R^{13}$ is hydrocarbyl or substituted hydrocarbyl, and $R^{14}$ is hydrocarbyl or substituted hydrocarbyl.

20. A transition metal complex of a compound of the formula

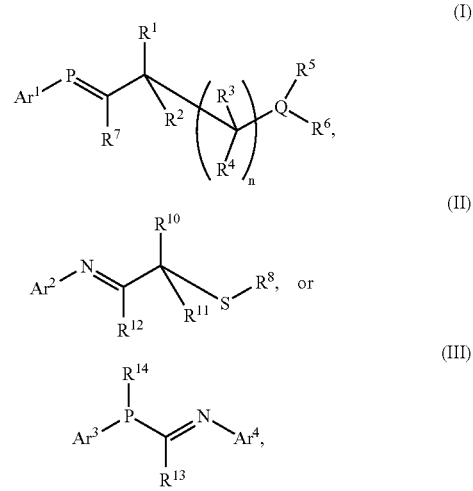

wherein:

$Ar^1$, $Ar^2$, $Ar^3$ and $Ar^4$ are each independently aryl or substituted aryl;

$R^7$ is hydrogen, hydrocarbyl or substituted hydrocarbyl;

Q is sulfur, oxygen, nitrogen or phosphorous;

n is 0 or 1;

when n is 0 and Q is oxygen or sulfur, $R^1$ and $R^2$ are each independently hydrogen, hydrocarbyl, substituted hydrocarbyl or $R^1$ and $R^2$ taken together form a ring, $R^6$ is not present and $R^5$ is hydrocarbyl or substituted hydrocarbyl;

when n is 1 and Q is oxygen or sulfur, $R^1$, $R^2$, $R^3$ and $R^4$ taken together form an aromatic ring which may be substituted, $R^6$ is not present and $R^5$ is hydrocarbyl or substituted hydrocarbyl;

when n is 0 and Q is nitrogen, $R^1$, $R^2$, $R^5$, $R^6$ and said nitrogen together form an aromatic ring, or $R^1$ is hydrogen, hydrocarbyl or substituted hydrocarbyl, $R^2$ and $R^5$ taken together are part of a double bond, and $R^6$ is aryl or substituted aryl;

when n is 1 and Q is nitrogen, $R^1$ is hydrogen, hydrocarbyl or substituted hydrocarbyl, $R^1$, $R^2$ and $R^3$ are each independently hydrogen, hydrocarbyl or substituted hydrocarbyl provided that any two of $R^1$, $R^2$ and $R^3$ geminal or vicinal to each other together may form a ring, $R^4$ and $R^5$ taken together are part of a double bond, and $R^6$ is aryl or substituted aryl;

when n is 0 and Q is phosphorous $R^1$ and $R^2$ are each independently hydrogen, hydrocarbyl or substituted hydrocarbyl, provided that $R^1$ and $R^2$ taken together may form a ring, and $R^5$ and $R^6$ are each independently hydrocarbyl or substituted hydrocarbyl;

when n is 1 and Q is phosphorous, $R^1$, $R^2$, $R^3$ and $R^4$ taken together form an aromatic ring which may be substituted, and $R^5$ and $R^6$ are each independently hydrocarbyl or substituted hydrocarbyl;

$R^8$ is hydrocarbyl or substituted hydrocarbyl;

$R^{10}$, $R^{11}$ and $R^{12}$ are each independently hydrogen, hydrocarbyl or substituted hydrocarbyl;

$R^{13}$ hydrogen, hydrocarbyl or substituted hydrocarbyl; and $R^{14}$ is hydrocarbyl or substituted hydrocarbyl;

wherein said transition metal is Fe, Co, Ni or Pd;

and provided that when said transition metal is Pd, when n is 0 and Q is nitrogen $R^1$, $R^2$, $R^5$, $R^6$ and said nitrogen together do not form an aromatic ring.

21. The complex as recited in claim 20 wherein only 1 molecule of said ligand is coordinated to an atom of said transition metal.

22. The complex as recited in claim 21 wherein said transition metal is Pd or Ni.

23. The complex as recited in claim 22 wherein said ligand is (I).

24. The complex as recited in claim 23 wherein:

$Ar^1$ is phenyl or substituted phenyl;

$R^7$ is hydrogen;

when n is 0 and Q is oxygen or sulfur, $R^1$ and $R^2$ are both hydrogen, and $R^5$ is alkyl or substituted alkyl;

when n is 1 and Q is oxygen or sulfur, $R^1$, $R^2$, $R^3$ and $R^4$ taken together form a benzene ring, and $R^5$ is alkyl or substituted alkyl;

when n is 0 and Q is nitrogen, $R^1$, $R^2$, $R^5$, $R^6$ and said nitrogen together form a 2-pyridyl ring (group), or $R^1$ is phenyl or substituted phenyl, and $R^6$ is phenyl or substituted phenyl;

when (I) is present, n is 0 and Q is phosphorous, $R^1$ and $R^2$ are both hydrogen, and $R^5$ and $R^6$ are each independently phenyl or substituted phenyl, and when n is 1 and Q is phosphorous, $R^1$, $R^2$, $R^3$ and $R^4$ taken together form a benzene ring, and $R^5$ and $R^6$ are each independently aryl or substituted aryl.

25. The complex as recited in claim 22 wherein said ligand is (II).

26. The complex as recited in claim 25 wherein $Ar^2$ is phenyl or substituted phenyl, wherein $R^{12}$ is hydrogen, $R^{10}$ and $R^{11}$ are each independently hydrocarbyl or substituted hydrocarbyl, and $R^8$ is phenyl or substituted phenyl.

27. The compound as recited in claim 22 wherein said ligand is (III).

28. The complex as recited in claim 27 wherein $Ar^3$ and $Ar^4$ are each independently phenyl or substituted phenyl, $R^{13}$ is hydrocarbyl or substituted hydrocarbyl, and $R^{14}$ is hydrocarbyl or substituted hydrocarbyl.

* * * * *